US012622667B2

(12) United States Patent
Kuenen et al.

(10) Patent No.: US 12,622,667 B2
(45) Date of Patent: May 12, 2026

(54) FLOW ASSESSMENT

(71) Applicant: KONINKLIJKE PHILIPS N.V., Eindhoven (NL)

(72) Inventors: Maarten Petrus Joseph Kuenen, Veldhoven (NL); Brian Brand Antonius Johannes Bloemendal, Helenaveen (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/709,877

(22) PCT Filed: Oct. 20, 2022

(86) PCT No.: PCT/EP2022/079155
§ 371 (c)(1),
(2) Date: May 14, 2024

(87) PCT Pub. No.: WO2023/088632
PCT Pub. Date: May 25, 2023

(65) Prior Publication Data
US 2025/0017551 A1　Jan. 16, 2025

(30) Foreign Application Priority Data

Nov. 17, 2021　(EP) ..................................... 21208674
Mar. 25, 2022　(EP) ..................................... 22164513

(51) Int. Cl.
*A61B 8/06* (2006.01)
*A61B 8/00* (2006.01)
(Continued)

(52) U.S. Cl.
CPC .................. *A61B 8/06* (2013.01); *A61B 8/02* (2013.01); *A61B 8/12* (2013.01); *A61B 8/488* (2013.01); *A61B 8/5223* (2013.01)

(58) Field of Classification Search
CPC .... A61B 8/06; A61B 8/02; A61B 8/12; A61B 8/488; A61B 8/5223; A61B 8/4254;
(Continued)

(56) References Cited

U.S. PATENT DOCUMENTS

2008/0119736 A1* 5/2008 Dentinger .............. A61B 8/488
600/443
2013/0303907 A1* 11/2013 Corl ...................... A61B 8/488
600/443

FOREIGN PATENT DOCUMENTS

WO　　　2017129495 A1　8/2017
WO　WO-2020207883 A1 * 10/2020 ............. A61B 8/461

OTHER PUBLICATIONS

International Search Report and Written Opinion of PCT/EP2022/079155, dated Jan. 25, 2023.

* cited by examiner

*Primary Examiner* — Kaitlyn E Sebastian

(57)　　　　　　　　ABSTRACT

The present invention relates to flow measurement in a vessel. In order to provide a facilitated and less complex determination of the average peak velocity based solely on a plurality of ultrasound signals, a device (10) for flow measurement in a vessel is provided that comprises a data input (12), a processor (14) and an output interface (16). The data input is configured to provide a plurality of ultrasound signals that relate to blood flow within the vessel. The processor is configured to generate blood flow velocity data based on the plurality of ultrasound signals; to detect a measure for similarity or variation based on the plurality of ultrasound signals; to ascertain a pulse rate based on the
(Continued)

detected measure for similarity or variation; and to compute, based on the estimated pulse rate, an average parameter value for a blood flow parameter, which blood flow parameter is generated from the plurality of ultrasound signals. The output interface is configured to provide the average parameter value to a user for further assessment.

14 Claims, 4 Drawing Sheets

(51) Int. Cl.
    *A61B 8/02*          (2006.01)
    *A61B 8/08*          (2006.01)
    *A61B 8/12*          (2006.01)

(58) Field of Classification Search
    CPC ... A61B 8/4263; A61B 8/5261; A61B 8/4245;
                                    A61B 8/5207
    See application file for complete search history.

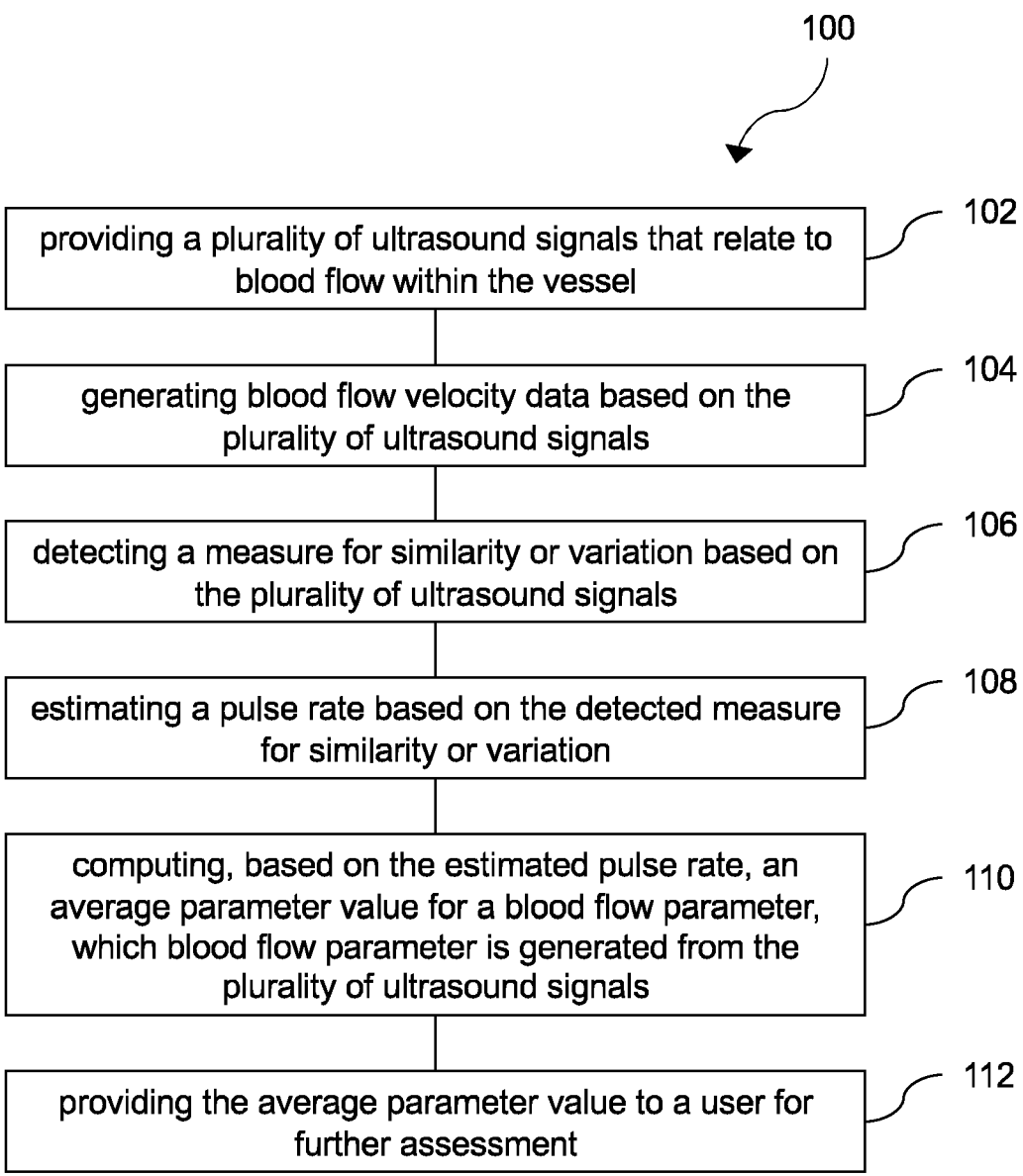

100 providing a plurality of ultrasound signals that relate to blood flow within the vessel — 102 generating blood flow velocity data based on the plurality of ultrasound signals — 104 detecting a measure for similarity or variation based on the plurality of ultrasound signals — 106 estimating a pulse rate based on the detected measure for similarity or variation — 108 computing, based on the estimated pulse rate, an average parameter value for a blood flow parameter, which blood flow parameter is generated from the plurality of ultrasound signals — 110 providing the average parameter value to a user for further assessment — 112

Fig. 3

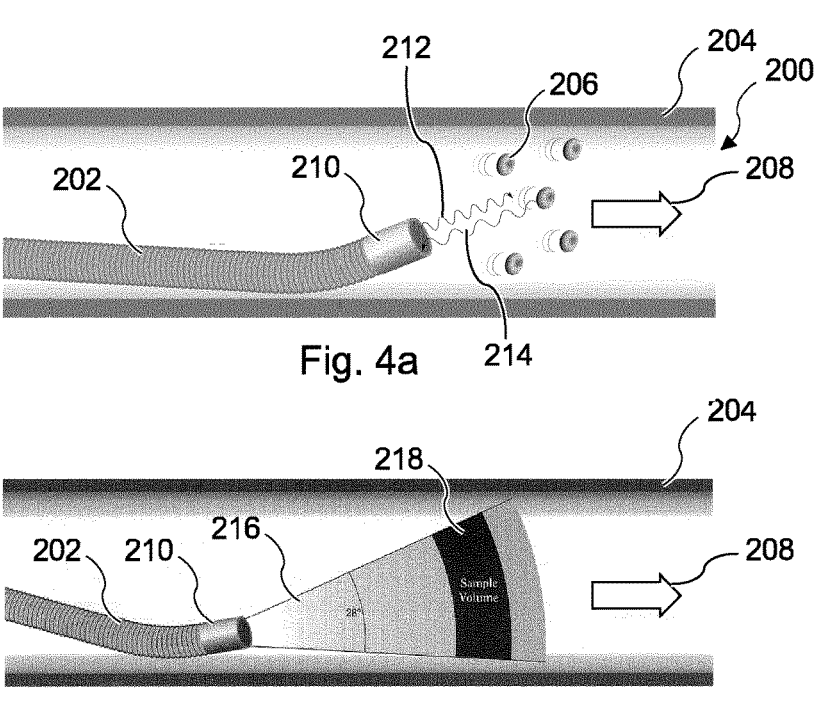
Fig. 4a
Fig. 4b
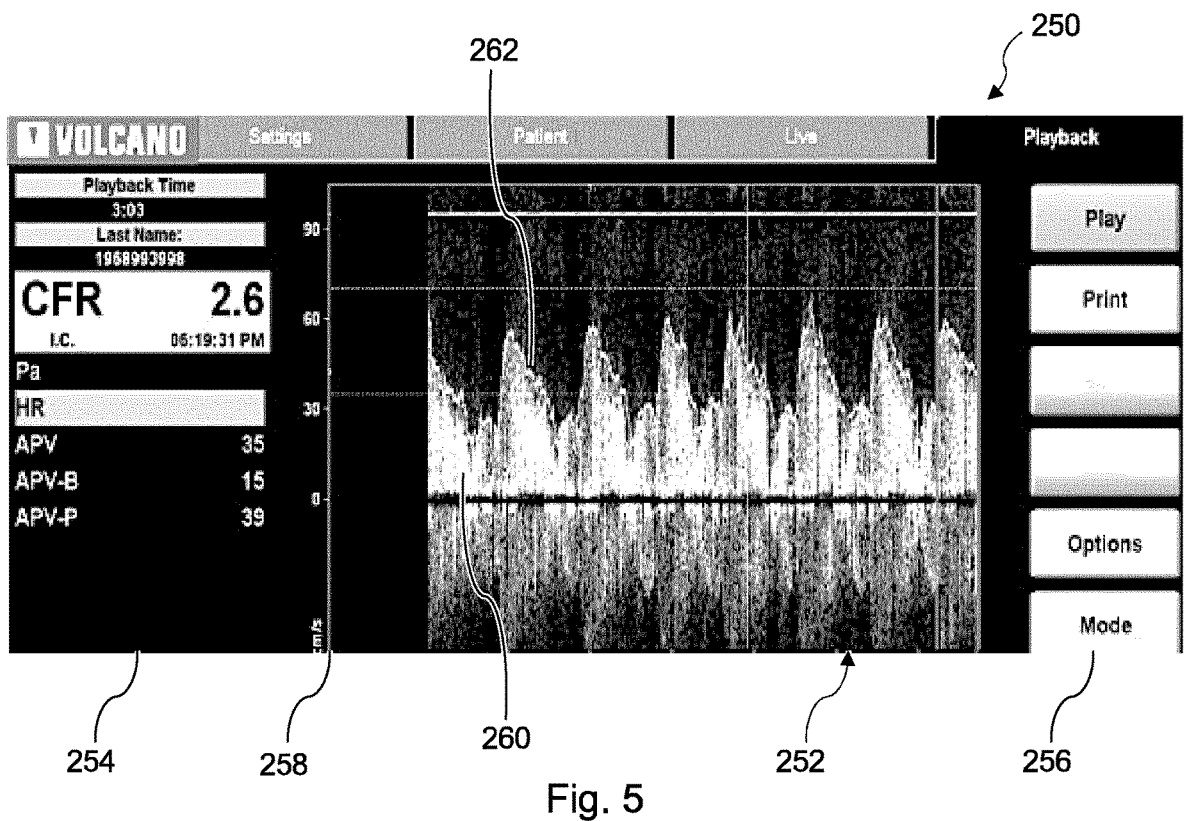
Fig. 5

FLOW ASSESSMENT

REFERENCE TO RELATED APPLICATIONS

This application is the U.S. National Phase application under 35 U.S.C. § 371 of International Application No. PCT/EP2022/079155, filed on Oct. 20, 2022, which claims the benefit of the filing date of European Patent Application No. 21208674.8, filed Nov. 17, 2021, and European Patent Application No. 22164513.8, filed Mar. 25, 2022. These applications are hereby incorporated herein by reference.

FIELD OF THE INVENTION

The present invention relates to flow measurement in a vessel and relates in particular to a device for flow measurement in a vessel, to a system for flow measurement in a vessel and to a method for flow measurement in a vessel.

BACKGROUND OF THE INVENTION

As an example, assessing the hemodynamic significance of cardiovascular and peripheral vascular disease by intravascular flow measurement has been shown beneficial to guide treatment of circulatory disease. Especially, in the coronary arteries, large clinical trials have proven that decision-making based on pressure and flow measurements may improve clinical outcome compared to angiography alone. Flow measurements may be provided in case of non-obstructive coronary artery disease, e.g. angina complaints without visible obstructions in the large arteries. Additionally, beyond diagnostics, blood flow monitoring during embolization interventions may be provided for assessing the degree of embolization and guiding when to stop to prevent embolization of healthy tissue, for example in transarterial chemoembolization (TACE).

As an example for assessing blood flow velocity, guide wires with a Doppler ultrasound sensor were developed more than two decades ago that are equipped with a single element lead zirconate titanate (PZT) ultrasound transducer. With these devices, an electrical driving pulse can be sent to the PZT which emits an ultrasound pulse, and a reflected ultrasound pulse is received by the PZT, which is converted to electrical signal. By analysis of the difference between the sent and received signals, the blood velocity in a specific sampling area can be deduced as in standard ultrasound pulsed Doppler measurements.

Based on this, instantaneous peak velocity (IPV) in the vessel is determined at each point in time. An average peak velocity (APV) is obtained by averaging the IPV over one or more cardiac cycles, and the APV is used as a surrogate for the flow. The assessment of the APV from the IPV requires the IPV to be averaged over one or more heart cycles. This information is provided from an auxiliary signal, i.e. the electrocardiogram (ECG). The R-peak in the ECG is estimated as feature point to denote the onset of each heart cycle. This allows selection of the samples of the IPV signal that need to be averaged to calculate the APV. However, it has been shown that this means additional effort that increases the overall complexity.

SUMMARY OF THE INVENTION

There may thus be a need to provide a facilitated and less complex estimation of the average peak velocity information.

The object of the present invention is solved by the subject-matter of the independent claims; further embodiments are incorporated in the dependent claims. It should be noted that the following described aspects of the invention apply also for the device for flow measurement in a vessel, for the system for flow measurement in a vessel and for the method for flow measurement in a vessel.

According to the present invention, a device for flow measurement in a vessel is provided. The device comprises a data input, a processor and an output interface. The data input is configured to provide a plurality of ultrasound signals that relate to blood flow within the vessel. The processor is configured to generate blood flow velocity data based on the plurality of ultrasound signals. The processor is also configured to detect a measure for similarity or variation based on the plurality of ultrasound signals. The processor is further configured to estimate a pulse rate based on the detected measure for similarity or variation. The processor is furthermore configured to compute, based on the estimated pulse rate, an average parameter value for a blood flow parameter, which blood flow parameter is generated from the plurality of ultrasound signals. The output interface is configured to provide the average parameter value to a user for further assessment.

In an example, the plurality of ultrasound signals is provided as ultrasound Doppler signals.

As an effect, a facilitated and less complex estimation of the APV information is provided e.g. automatically and exclusively from the plurality of ultrasound signals, e.g. the ultrasound Doppler signals, without requiring auxiliary signals such as ECG, or even any user input.

According to an example, a display is provided. The processor is configured to output to the display the average parameter value.

According to an example, the processor is configured to apply an autocorrelation scheme to the plurality of ultrasound signals to determine a dependency of the signals and to generate time-related average values for the blood flow parameter.

According to an example, for the blood flow parameter, the processor is configured to estimate peak velocities in the vessel for a sequence of points in time based on the blood flow velocity data. For computing the average parameter value, based on the estimated peak velocities and the derived pulse rate, the processor is configured to generate an average peak velocity.

According to an example, the processor is configured to base the estimation of the heart cycle periods on the estimated peak velocities.

According to an example, the data input is configured to provide the plurality of ultrasound signals as obtained as a plurality of ultrasound signals from an ultrasound transducer of an interventional device. The plurality of ultrasound signals originates from a plurality of positions within the vessel. The processor is configured to ascertain flow velocity spectra over a range of locations comprising the plurality of positions within the vessel for the generation of the blood flow velocity data.

According to an example, the plurality of ultrasound signals is provided as a data stream and the processor is configured to generate the average parameter as realtime assessment.

According to the present invention, also a system for flow measurement in a vessel is provided. The system comprises a device for flow measurement according to one of the preceding examples. The system also comprises an interventional device with an ultrasound transducer attached to a distal portion of the interventional device. The interventional device is at least data-connected to the device for flow measurement. The ultrasound transducer generates the plurality of ultrasound signals, which are provided to the data input.

According to the present invention, also a method for flow measurement in a vessel is provided. The method comprises the following steps:

providing a plurality of ultrasound signals that relate to blood flow within the vessel;

generating blood flow velocity data based on the plurality of ultrasound signals;

detecting a measure for similarity or variation based on the plurality of ultrasound signals;

estimating a pulse rate based on the detected measure for similarity or variation;

computing, based on the estimated pulse rate, an average parameter value for a blood flow parameter, which blood flow parameter is generated from the plurality of ultrasound signals; and providing the average parameter value to a user for further assessment.

According to an aspect, ultrasound signals are provided and used to estimate a time-related parameter such as the pulse rate in order to use this parameter to compute an average value for a flow parameter. Hence, the ultrasound signals are used for i) providing the flow signals themselves, and for ii) indirectly providing the time related parameter value, which is then used for generating third data in form of a flow parameter average parameter.

According to an aspect, improvements in ultrasound based blood flow velocity measurements are provided. In an example, it is provided to estimate the average peak velocity exclusively from ultrasound Doppler signals without requiring auxiliary signals such as electrocardiogram. Thus, assessment of average peak flow velocity in intravascular Doppler flow measurement is provided.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 3 shows steps of an example of a method for flow measurement.

FIG. 4a and FIG. 4b schematically show longitudinal cross sections through a vessel with an inserted ultrasound device.

FIG. 5 shows an example of a user interface indicating velocity measurement.

DETAILED DESCRIPTION OF EMBODIMENTS

Figure 1:
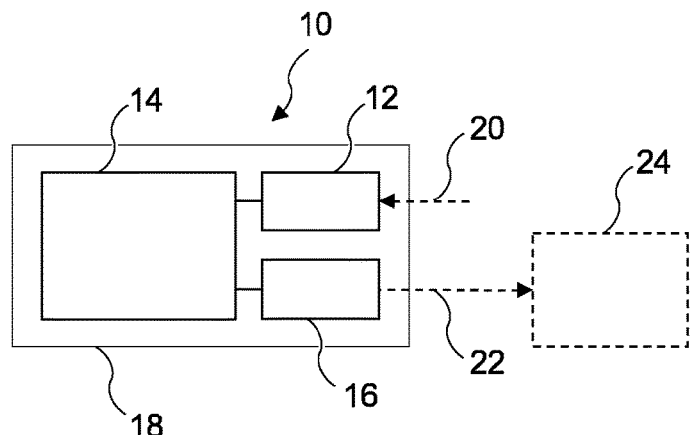
FIG. 1 schematically shows an example of a device for flow measurement in a vessel.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

FIG. 1 shows an example of a device 10 for flow measurement in a vessel. The device 10 comprises a data input 12, a processor 14 and an output interface 16. The data input 12 is configured to provide a plurality of ultrasound signals that relate to blood flow within the vessel. The processor 14 is configured to generate blood flow velocity data based on the plurality of ultrasound signals. The processor 14 is also configured to detect a measure for similarity or variation based on the plurality of ultrasound signals. The processor 14 is further configured to estimate a pulse rate based on the detected measure for similarity or variation. The processor 14 is furthermore configured to compute, based on the estimated pulse rate, an average parameter value for a blood flow parameter, which blood flow parameter is generated from the plurality of ultrasound signals. The output interface 16 is configured to provide the average parameter value to a user for further assessment.

The data input 12, the processor 14 and the output interface 16 can be provided in a common housing, indicated with a frame 18, or as separate components (not shown in detail). The data input 12, the processor 14 and the output interface 16 can also be provided in an integrated manner as partitions of a data processing module structure.

A first arrow 20 indicates the data supply, i.e. the plurality of ultrasound signals. A second arrow 22 indicates the provision of the generated data.

As an option, FIG. 1 shows a display 24 that is provided: The processor 14 may be configured to output the average parameter value to the display 24. Alternatively or additionally, the output of the average parameter value may be in audible form on an output device suitable for such purpose.

The term "data input" relates to providing the plurality of ultrasound signals. The data input can also be referred to as data input module. The data input can also be referred to as data supply, as image supply, as image data supply, as input unit or simply as input. In an example, the data input is data-connectable to an ultrasound imaging source arrangement like an ultrasound system, e.g. an external ultrasound imager or an ultrasound transducer arranged on a device configured to be inserted into a lumen of a subject or an object, for example on an interventional device introducible into a vascular structure. The ultrasound imaging source arrangement is configured for providing the ultrasound image data of the subject which is used for the detection/measuring steps. In an example, the image data input is data-connectable to a data storage having stored the plurality of ultrasound signals.

The term "processor" relates to data processing of the plurality of ultrasound signals. The processor, or data processor, can also be referred to as data processing module. The processor can also be referred to as data processing arrangement, as processor unit or as processor. In an example, the processor is data-connected to the image data input and the output interface.

The term "output interface" relates to providing the generated data for further purposes. The output interface can also be referred to as output interface module. The output interface can also be referred to as output or output unit. In an example, the output interface is data-connectable to a display arrangement or display device. In another example, the output is data-connected to a display.

As an example, for estimating the pulse rate, a heart cycle period is estimated based on the detected measure for similarity or variation to derive the pulse rate.

In an example, a heart cycle is estimated by identifying features that are indicative of a heart activity, which is mainly shown in form of a repetitive pattern of peaks or valleys or the like. These peaks (or valleys) are caused by the heart's activity. The first step is the identification of the similarity of variation in the ultrasound signals, i.e. the ultrasound data or ultrasound images. Then, the relation to time is established, e.g. this is done instantaneously. The "pulse rate" is the basic parameter of an ECG, which is not measured separately, but which information is derived from the ultrasound (image) data.

Figure 2:
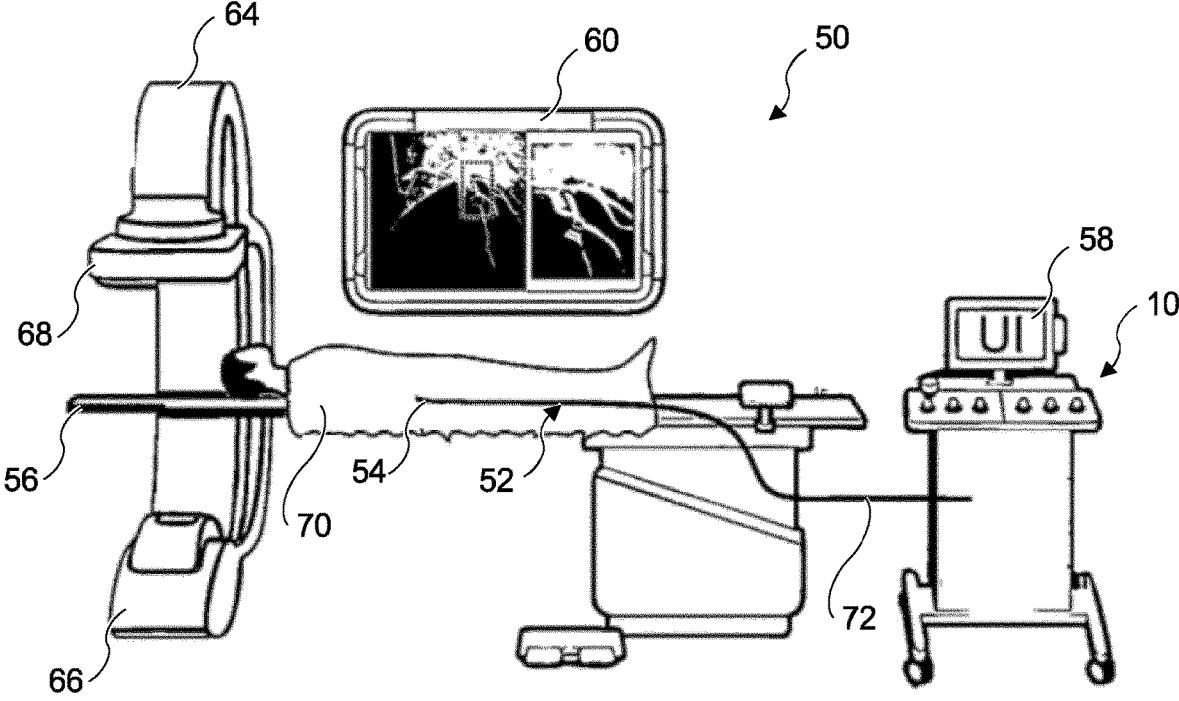
FIG. 2 schematically shows an example of a system for vessel flow measurement.

FIG. 2 shows an example of a system 50 for flow measurement in a vessel. The system 50 comprises an example of the device 10 for flow measurement according to one of the preceding and following examples. Further, an interventional device 52 with an ultrasound transducer 54 attached to a distal portion of the interventional device 52 is provided. The interventional device 52 is at least data-connected to the device 10 for flow measurement. The ultrasound transducer 54 generates the plurality of ultrasound signals, which are provided to the data input (not shown in detail).

As an option, FIG. 2 shows a subject support 56, e.g. a patient table.

The device 10 for flow measurement may be provided as a movable control console and may be equipped with a graphical user interface 58 like a display and further control elements. Still further, a monitor arrangement 60 is provided in the vicinity of the patient support 56, such as a ceiling- or wall-mounted display. As a further option, additional imaging systems are provided, like an X-ray imaging system 64 with an X-ray source 66 and an X-ray detector 68 mounted to a movably supported C-arm structure. An object of interest, like a subject 70, can be arranged on the subject support 56. The subject 70 is shown with cover drapes. A line 72 indicates the data-connection, which can be wired connection or wireless connection.

The exemplary system illustrated in FIG. 2 indicates that the interventional device 52, such as the intravascular device (e.g. FloWire, ComboWire or pressure wire), is connected by a wired or a wireless connection to an apparatus, e.g. a console, or through a patient interface module to the console. The console may provide the electrical excitation pulse to the ultrasound transducer. Alternatively, the electrical excitation pulse could be provided by an autonomous electrical component that is integrated in the patient interface module. The proximal portion of the interventional device remains outside of the body of the patient during flow measurement and/or pressure measurement with the distal portion of the interventional device inserted into the anatomical structure of the patient, e.g. blood vessel.

In a further alternative, the electrical source is integrated in the proximal portion of the interventional device and is configured to communicate with an application specific integrated circuit (ASIC) located nearby the ultrasound transducer in the distal portion of the interventional device, which ASIC provides then the electrical excitation pulses for the ultrasound transducer.

Optionally, the measurement data can be transmitted wirelessly directly to a user interface such as a display.

In any of the embodiments, the processor 14 is involved in processing the measurement data to output the result of the flow or pressure measurement. The processor 14 may be integrated in at least one of the group of the console, the display and patient interface module. The measurement result may be presented on a user interface in the form of a visual representation (e.g. graphical and/or numerical), or it can be presented as acoustic signal, wherein the acoustic characteristics of the signal vary according to the output flow result.

The system 50, schematically illustrated in FIG. 2, may comprise in various alternative configurations the following components:

The interventional device, wherein the processor 14 is integrated within the proximal portion of the interventional device, further comprising a user interface for outputting the flow results, and wherein the processor 14 communicates through wireless communication with the user interface.

The interventional device in wired or wireless communication with a console that comprises the processor 14, and which outputs the flow result to the user interface, which user interface can be separate from or integrated in the console.

In any of the embodiments, the system may further comprise at least an extracorporeal apparatus suitable for providing at least one of the imaging modalities: X-ray angiography, computer tomography, ultrasound imaging and magnetic resonance imaging.

FIG. 3 shows steps of an example of a method 100 for flow measurement. The method 100 comprises the following steps: in a first step 102, a plurality of ultrasound signals is provided that relate to blood flow within the vessel. In a second step 104, blood flow velocity data is generated based on the plurality of ultrasound signals. In a third step 106, a measure for similarity or variation is detected based on the plurality of ultrasound signals. In a fourth step 108, a pulse rate is estimated based on the detected measure for similarity or variation. In a fifth step 110, based on the estimated pulse rate, an average parameter value for a blood flow parameter is computed, which blood flow parameter is generated from the plurality of ultrasound signals. In a sixth step 112, the average parameter value is provided to a user for further assessment.

The term "ultrasound signals" relates to blood flow related data acquired by ultrasound imaging.

The term "blood flow velocity data" relates to data indicative or representing the flow of blood inside the vessel.

The term "measure for similarity or variation" relates to identifying repetitive patterns that may stand for a dependency of the plurality of signals over time. For example, similarities may be provided as higher peaks or as lower bottom parts of a measured curve of the signals. For example, variation may relate to different inclination rates or descending factors of a curve.

The term "blood flow parameter" relates to various parameter that are of interest in connection with blood flow assessment. For example, as a blood flow parameter, blood flow velocity, velocity distribution, flow characteristics, pressure, pressure distribution and the like are provided.

The term "average parameter value" relates to a mean value of the parameter that may change over time.

The pulse rate, based on the heart cycle periods, can for example be estimated from the instantaneous peak velocity (IPV) signal. In other embodiments, different intermediate signals in the Doppler processing chain may be used, such as for example the Doppler audio signal, signals (such as energy) derived from sub-bands of the Doppler spectrum, or other features estimated that can be derived.

In an example, for the detecting of the measure for similarity or variation, it is provided the step of detecting of a measure for similarity or variation of the blood flow velocity data.

In an example, peaks are identified in the blood flow velocity data, and periodicity is estimated based on the identified peaks.

In an example, the detecting of the measure for similarity or variation comprises estimating heart cycle periods based on the plurality of ultrasound signals to derive the pulse rate.

In an example of the method, an autocorrelation scheme is applied to the plurality of ultrasound signals to determine a dependency of the signals and to generate time-related average values for the blood flow parameter.

In an example, based on the detecting of the measure for similarity or variation, the autocorrelation scheme is applied to the plurality of ultrasound signals.

In an example, for the blood flow parameter, it is provided the step of estimating peak velocities in the vessel for a sequence of points in time based on the blood flow velocity data.

The term autocorrelation relates to a correlation provided within the plurality of signals. The autocorrelation comprises context information. For example, heart cycle information may be provided as context information present within the ultrasound signals.

In an example, autocorrelation is applied on a time segment of a signal, e.g. the IPV, and a curve is obtained whose peaks are located at a time lag corresponding to integer multiples of main period of the original signal. Detection of the peak location from the autocorrelation output thus leads to detection of the period from the IPV signal.

In an example of the method, for the blood flow parameter, it is provided the step of estimating peak velocities in the vessel for a sequence of points in time based on the blood flow velocity data; and, for computing the average parameter value, based on the estimated peak velocities and the derived pulse rate, an average peak velocity is generated.

In an example, flow velocity spectra are sampled from the plurality of ultrasound signals.

In an example, the estimated peak velocities are provided as instantaneous peak velocities.

In an example, the average peak velocity is generated for one or more of the estimated heart cycle periods.

The average peak velocity is generated for a time period or time span that is related to the estimated heart cycle periods or the estimated heart cycle rates.

In an example, the peak velocities are assigned to heart cycles based on the estimated heart cycle periods and the average peak velocity is generated for a determined whole number of heart cycles, i.e. for one heart cycle, or more than one, like two, three, four, five or even more heart cycles.

As an example, using whole periods results in an APV signal that does not feature periodicity with the heart cycle duration. If a non-integer value, e.g. 1.5, would be used, the APV signal would still be period with the heart cycle duration. Generally, the closer to an integer value, the more stable the APV will be, e.g. averaging over 2.9 heart cycles would be better than over 2.7 heart cycles.

In a further example, the APV is obtained using a low-pass filter that removes all frequencies that are integer multiples of the pulse rate. In an example, a moving average filter is provided as an effective implementation. In another option, other low-pass filters are provided, e.g. infinite impulse response or IIR filters, with a similar property.

In an example, five to eight cardiac cycles are considered for determining the average peak velocity level.

In another example, three cardiac cycles are considered for determining the average peak velocity level. This allows a sufficient degree of stability in terms of respiratory variations, and it also allows sufficient speed or reactivity in situations where the coronary blood flow changes quickly.

In an example, a window for selecting the estimated peak velocity values is provided that is fixated to the cardiac cycle.

In an example, a peak velocity curve is generated based on the estimated peak velocities; and wherein the average peak velocity is generated based on the peak velocity curve.

In an option, the average peak velocity is generated based on the estimated peak velocities.

According to an example, not shown in detail in FIG. 1 or FIG. 2, the processor 14 is configured to apply an autocorrelation scheme to the plurality of ultrasound signals to determine a dependency of the signals and to generate time-related average values for the blood flow parameter.

According to an example, not shown in detail in FIG. 1 or FIG. 2, for the blood flow parameter, the processor 14 is configured to estimate peak velocities in the vessel for a sequence of points in time based on the blood flow velocity data. For computing the average parameter value, based on the estimated peak velocities and the derived pulse rate, the processor 14 is configured to generate an average peak velocity.

According to an example, not shown in detail in FIG. 1 or FIG. 2, the processor 14 is configured to base the estimation of the heart cycle periods on the estimated peak velocities.

According to an example, not shown in detail in FIG. 1 or FIG. 2, the data input 12 is configured to provide the plurality of ultrasound signals as ultrasound data obtained within the vessel.

According to an example, not shown in detail in FIG. 1 or FIG. 2, the data input 12 is configured to provide the plurality of ultrasound signals as a plurality of ultrasound Doppler signals relating to blood flow in a sample volume. The sample volume can also be referred to as sample area.

According to an example, not shown in detail in FIG. 1 or FIG. 2, the data input 12 is configured to provide the plurality of ultrasound signals as obtained as a plurality of ultrasound signals from an ultrasound transducer of an interventional device. The plurality of ultrasound signals originates from a plurality of positions within the vessel. Further, the processor 14 is configured to ascertain flow velocity spectra over a range of locations comprising the plurality of positions within the vessel for the generation of the blood flow velocity data.

The plurality of positions can also be referred to as a plurality of distances, The range of locations can also be referred to as range of depths.

According to an example, not shown in detail in FIG. 1 or FIG. 2, the plurality of ultrasound signals is provided as a data stream, and the processor 14 is configured to generate the average parameter as realtime assessment.

According to an example, not shown in detail in FIG. 1 or FIG. 2, the processor 14 is configured to provide the average parameter value single-source based. In other words, the processor 14 is supplied with data from only one source.

According to an example, not shown in detail in FIG. 1 or FIG. 2, the processor 14 is configured to provide a data verification loop. The processor 14 is also configured to determine a quality of the flow data. The quality of the flow data is for example the quality of the blood flow velocity data that is based on the plurality of ultrasound signals and/or the quality of the average parameter value for the blood flow parameter.

In an example of the method, the estimating of the heart cycle periods is based on the estimated peak velocities.

In an example of the method, the plurality of ultrasound signals is provided as ultrasound data obtained within the vessel.

As an example, the plurality of ultrasound signals is provided as ultrasound data acquired internally of the vessel.

In an alternative or additional option, the plurality of ultrasound signals is provided as ultrasound data obtained from outside the vessel. As an example, the plurality of ultrasound signals is provided as ultrasound data acquired externally of the vessel.

In an example of the method, the plurality of ultrasound signals is provided as a plurality of ultrasound Doppler signals relating to blood flow in a sample volume.

In an example, provided as an option, one Doppler signal is provided as the plurality of ultrasound signals. The one Doppler signal is relating to blood flow in a sample volume.

In an example of the method, the plurality of ultrasound signals is obtained as a plurality of ultrasound signals from an ultrasound transducer of an interventional device; the plurality of ultrasound signals originates from a plurality of positions within the vessel; and the generating of the blood flow velocity data comprises ascertaining flow velocity spectra over a range of locations comprising the plurality of positions within the vessel.

In an example of the method, the plurality of ultrasound signals is provided as a data stream and the generating of the average parameter is provided as realtime assessment.

The term "realtime" relates to providing the assessment essentially without delay, e.g. with a delay of maximum ten heart cycles, e.g. maximum of five heart cycles.

For example, the average parameter value is provided based on the last ten, or less than ten, e.g. five, four or three seconds.

In an example of the method, the average parameter value is provided single-source based.

The average parameter value is based on one data source only (single source), namely the provision of ultrasound data. While the ultrasound data comprises the information that can be used for determining blood flow related parameters, the ultrasound data also comprises the information that allows to retrieve the heart cycle information that can then be used for retrieving average values for a heart cycle. Thus, while providing a facilitated measuring setup with a single sensor, i.e. the ultrasound transducer, more than just one information is made available to the user.

In an example of the method, a data verification loop is provided. Further, it is provided the step of determining a quality of the flow data. The quality of the flow data is for example the quality of the blood flow velocity data that is based on the plurality of ultrasound signals and/or the quality of the average parameter value for the blood flow parameter.

In an example, a guidance for a user is provided on the reliability of the data, i.e. the reliability of the quality of the measurement.

In an example, a measurement of average peak flow velocity (APV) is provided that enables measurement of APV using only a Doppler wire and requires no additional signals. A secondary gating signal, e.g. electrocardiogram or ECG, is not required. An autocorrelation scheme is provided to derive heartbeat information that is used to calculate the APV from the IPV. As an example, heartbeat information is extracted from the Doppler ultrasound data itself, such that no secondary gating signal is required. In an option, this approach also enables estimation of auxiliary physiological signals, such as heart rate variability or respiration rate, from the measurement.

According to an aspect, in an example, a system is provided that comprises:

an intravascular device (e.g. guidewire or catheter) with one or more ultrasound elements (e.g. PZT, CMUT, PMUT, PVDF));

a wired or wireless connection between intravascular device and acquisition electronics;

acquisition and/or control electronics (e.g. console of patient interface module) comprising at least one processor configured for at least one of: analog preprocessing, digitization, and means for digital processing of signals measured by intravascular device; and a software (preferably running in real-time) for flow signal processing, comprising: flow velocity spectrum estimation (e.g. using pulsed-wave Doppler processing), IPV estimation from the flow velocity spectrum, heart cycle period estimation from flow velocity information and APV estimation from the IPV and heart cycle period.

In an example, an apparatus for flow measurement in a vessel is provided that comprises a processor configured to:

obtain a plurality of ultrasound signals from an ultrasound transducer of an interventional device, wherein the plurality of ultrasound signals originates from a plurality of positions within the vessel;

ascertain flow velocity spectra over a range of locations comprising the plurality of positions within the vessel;

detect a measure for similarity or variation of the flow velocity spectra; and obtain a composite flow velocity spectrum over the plurality of positions within the vessel by suppressing interference components from the flow velocity spectra based on the measure for similarity or variation.

In another example, an apparatus for flow measurement in a vessel is provided that comprises a processor configured to:

obtain a plurality of ultrasound signals from an ultrasound transducer of an interventional device, wherein the plurality of ultrasound signals originates from a plurality of positions within the vessel;

ascertain a flow velocity spectrum over a range of locations comprising the plurality of positions within the vessel;

ascertain an instantaneous peak velocity from the flow velocity spectrum;

detect heart cycle period from the instantaneous peak velocity; and obtain an average peak velocity from the instantaneous peak velocity and the heart cycle period.

In an example, an autocorrelation-based algorithm is applied to estimate the pulse rate, or in fact, heart cycle period, from the IPV. This algorithm is causal with relatively low latency, allowing the pulse rate to be detected in real-time. In an example, an autocorrelation-based algorithm is applied based on WO 2017/129495 A1.

In other embodiments, alternative methods for estimating periodicity may be used, such as a Fourier transform or time-domain detection of the onset of specific phases in the heart cycle such as for example the systolic or diastolic flow phase.

Based on the real-time, instantaneous estimate of the heart cycle period, the APV can also be derived in real time, for example by averaging the IPV signal over the most recent n heart cycle periods, where n is an integer number, e.g. 1-5. A lower value of n results in a more instantaneous but potentially noisy APV, whereas a higher value of n results in a more smoothed and slightly delayed APV. Excessively high values of n result in too much smoothing, which may cause underestimation of the APV during peak flow conditions in hyperemia.

Figure 7:
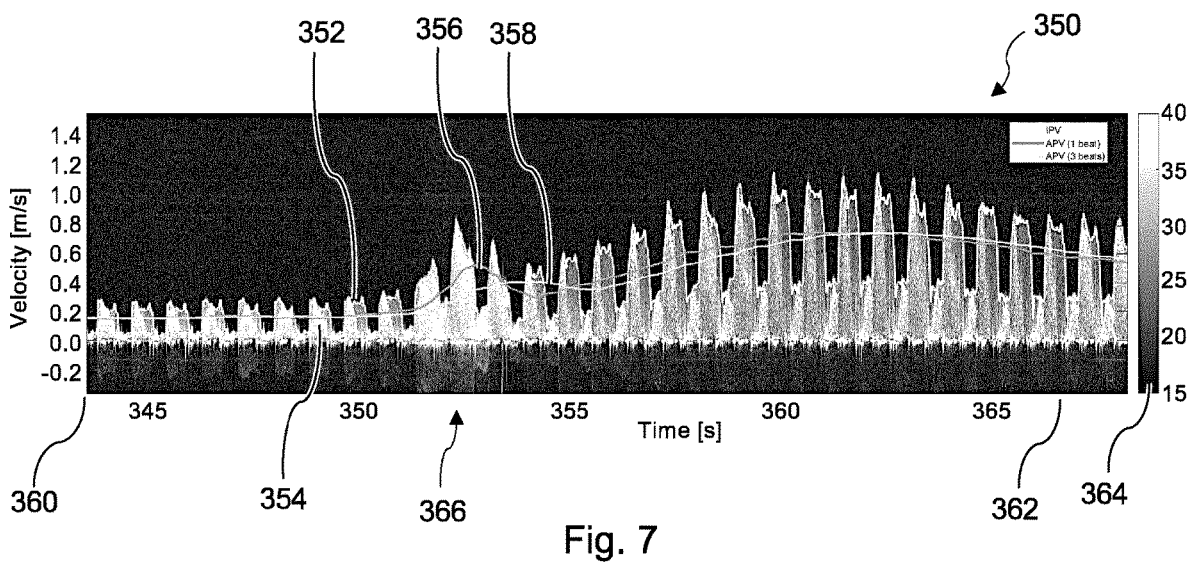
FIG. 7 shows a graph with IPV and two differently obtained APV signals overlaid to an ultrasound (Doppler) spectrum.

With the instantaneous pulse rate assessment, however, APV is instantaneously estimated on a sample-by-sample basis, i.e., at a higher temporal resolution that results in a relatively smooth APV curve over time (FIG. 7). This provides advantages over determining an onset of each heart cycle from a separate ECG R-peak, from which APV can be estimated on a beat-by-beat basis. Further, via down-sampling, i.e. taking only one estimated APV value per heart cycle period, a similar APV graph can be obtained as with a system having an external ECG signal.

In the use case of a coronary flow reserve (CFR) measurement, the aim is to measure the relative increase in APV from resting condition (baseline) to exercise condition (hyperemia, when the arterioles are maximally opened to provide as much blood and oxygen to the heart muscle as the body is capable of). The exercise condition is reproduced in the catheterization lab by injection (intravenous or intra-arterial) of adenosine or, alternatively, regadenoson or papaverine. In the intra-arterial use case, coronary flow is rapidly increased to a peak value in a matter of seconds and then slowly fades back to baseline conditions. For CFR measurement, the maximum APV level is required which can be obtained automatically by a running maximum algorithm after the user selects the initial baseline value. Given the baseline APV, the CFR value can then also be calculated, e.g. automatically.

Beyond the APV, additional physiological information, such as heart rate variability and respiration rate, can be extracted from the derived pulse rate.

In an example, information about the validity of the detected pulse rate/heart cycle period is provided to the user. Such validity information can be derived from intermediate signals of a pulse rate estimation algorithm. If the pulse rate is not considered valid (which may be due to a bad IPV signal used for estimation, or due to irregularities in the patient's heartbeat), feedback may be provided to the user in various forms. For example, the user may be instructed to optimize the flow signal prior to injection of adenosine for a CFR measurement. Another option would be to not display the APV value.

The possibility to measure heart rate in real time enables assessment of various physiological parameters and indices that can be derived from it. For example:

the heart rate itself tends to have a periodic behavior caused by cardio-pulmonary interaction. As such, the heart rate itself is modulated by the respiration rate, allowing estimation of the respiration rate as the fundamental frequency in the heart rate signal. Like with the estimation of heart rate, this may be pursued via an autocorrelation approach. This information about the respiration rate can be utilized in the accurate determination of the CFR, for example by using the same period in the respiration phase of the resting and hyperemic measurement or by using a correction factor to account for the effect of respiration on the APV;

the heart rate variability in itself is a clinically significant hemodynamic parameter that can be extracted from the heart rate signal;

specific pathophysiological conditions can be detected during the measurement (bradycardia, tachycardia, ectopic heart beats) and can be signaled and/or removed from the APV measurement to improve the accuracy of the APV and other parameters like CFR, index of microvascular resistance (IMR), hyperemic microvascular resistance (HMR), baseline hyperemic resistance (BMR), HMR/BMR and coronary flow capacity (CFC).

In an additional embodiment, the information about the validity of the heart rate is used to provide information about the reliability of the flow signal.

FIG. 4a and FIG. 4b schematically show cross sections through a vessel 200 with an inserted ultrasound device 202 as an example of an interventional device inside the blood vessel 200. The vessel 200 is indicated by vessel walls 204. Blood flow inside the vessel is indicated by blood cells 206 that move along the vessel in a blood flow direction 208. The ultrasound device 202 comprises a transducer 210 at its distal end. The transducer 210 emits ultrasound waves 212 and receives reflected waves 214 such that ultrasound data is generated and forwarded to the data input 12 (not shown in FIG. 4a) and the processor 214 respectively. FIG. 4b indicates an example for a field of view 218 of the transducer 210 with a resulting sample volume 218 in which the flow of blood is detected, i.e. measured.

FIG. 5 shows an example of a user interface 250 indicating velocity measurement. A central portion shows a graph 252, a left portion 254 indicates values and other type of information and a right portion 256 provides interaction parts for entry of user commands and the like.

A first vertical axis 258 of the graph 252 indicates velocity, while a horizontal axis indicates a time axis. The graph 252 provides peak velocities 260. Based on the peak velocities, similarity or variation can be identified and used for estimating cardiac cycles and thus pulse rate. It is noted that the dynamic properties of blood inside a vessel are always subject to heart activity and thus shows a relation to pulse rate. A first curve 262 is indicated that provides information about the IPV, i.e. the estimated peak velocity as function of time. The APV is numerically shown on the left-hand side and represents the average value of the first curve 262 over one or more consecutive cardiac cycles.

FIG. 5 indicates an example of flow velocity that is determined based on measurements with an interventional ultrasound imaging device. The distribution of velocities in the sample volume is shown in time as a grayscale image. One vertical line in the Doppler image describes the relative extent to which the velocity along the vertical axis is observed. The first curve 262 is the estimated instantaneous peak velocity (IPV) in the vessel at each point in time. The average peak velocity (APV) is obtained by averaging the IPV over one or more cardiac cycles, and the APV is used as a surrogate for the flow. The cardiac cycles are derived from the estimated instantaneous peak velocities.

Figure 6:
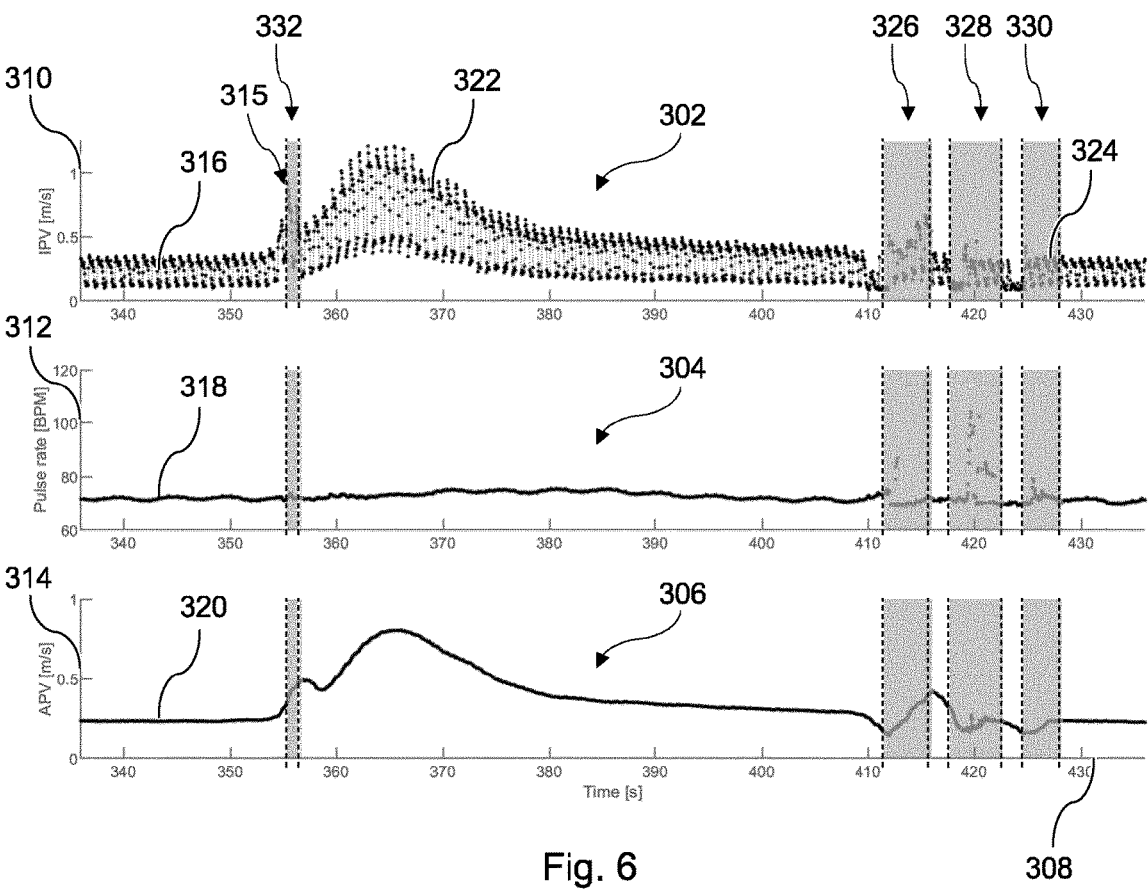
FIG. 6 shows an example for graphs indicating an estimation of an instantaneous peak velocity (IPV) in the upper part, a detected pulse rate in the middle part and an average peak velocity (APV) in the bottom part.

FIG. 6 shows an example for graphs indicating an estimation of an instantaneous peak velocity 302 in an upper part, a detected pulse rate 304 in a middle part and an average peak velocity 306 in a bottom part.

A horizontal axis 308 indicates the time. An upper vertical axis 310 in the upper part indicates instantaneous peak velocity (IPV). A middle vertical axis 312 in the upper part indicates pulse rate. A bottom vertical axis 314 in the upper part indicates average peak velocity (APV).

FIG. 6 shows graphs relating to signals measured before and after adenosine injection 315. The upper part of FIG. 6 shows an estimation indication 316 from the IPV. The middle part of FIG. 6 shows a pulse rate curve 318. The bottom part of FIG. 6 shows an APV curve 320. The APV was obtained by averaging the IPV over the last 3 heart cycles.

In the upper part, first data points 322, as well as the estimation indication 316, indicate a valid pulse rate detection; second data points 324 indicate that not all pulse rate validity criteria were satisfied. During the latter phases, the IPV signal is deemed not sufficiently stable to provide a reliable pulse rate estimate.

An example of the detected pulse rate based on the IPV value during a CFR measurement is shown in FIG. 6 (middle graph). In this example, pulse rate estimation by means of a real-time autocorrelation is implemented over a four-second buffer of the IPV data. Prior to calculation of the autocorrelation, the IPV data are decimated to 25 Hz and its running average over the last four seconds is subtracted. The autocorrelation is evaluated over a lag range of up to two seconds, covering heart rates of 30 beats/minute and higher. The heart cycle period can then in principle be detected as the lag time at which the autocorrelation is highest; however, as the autocorrelation can be prone to erroneous period detection at integer multiples of the true heart cycle period, an approach described in WO 2017/129495, is provided to prevent this. Further to this, second order polynomial interpolation is applied for a more precise detection of the heart cycle period, i.e. to increase the resolution of the autocorrelation method.

In FIG. 6, as an option, an indication of the validity can be provided. As an example, regions where the detected heart cycle period is not valid, are highlighted by indication pattern 326, 328, 330 and 332 in FIG. 6. The validity can be determined based on the estimated heart cycle period itself, as well as intermediate signals in the autocorrelation algorithm.

In an example, validity is determined by the following conditions, which must all be satisfied:

the detected peak must be significantly higher than the baseline in order to represent a truly periodic signal rather than noise or artifacts: the normalized autocorrelation at the peak period must be 0.4 above its baseline level (defined as the average of the normalized autocorrelation values at 0.75 and 1.25 times the peak period);

same as condition above but applied after low-pass filtering of the normalized autocorrelation data to ensure that the autocorrelation remains stable over time; in this example a first-order autoregressive filter is applied, i.e., $y[n]=0.955 \cdot y[n-1]+(1-0.955) \cdot x[n]$;

the energy in the IPV signal (after mean subtraction) must be sufficiently high if there is a realistic periodically varying IPV signal. This energy is available as the autocorrelation value at lag 0. It must be above a threshold that corresponds to the minimum natural periodic variation in the IPV. In this example, we set this threshold based on assuming worst-case IPV signal featuring a minimum sinusoidal peak-to-peak variation over a cardiac cycle of 5 cm/s. For a four-second buffer sampled at 25 Hz, i.e., over 100 samples, such variation would correspond to a zero-lag autocorrelation of 0.03125 (m/s) 2;

the relative variation in the detected period (expressed as the standard deviation relative to the mean) over the last 1.5 seconds must be less than 10% to guarantee a stable pulse rate;

the currently detected period may not deviate more than 10% from the average of the detected period over the last 1.5 seconds;

after (re) starting the heart cycle detection, the detected period must be such that at least 3 heartbeats were already observed before the detected period can be considered valid.

In an additional embodiment, the injection of the hyperaemia-inducing substance can be automatically detected from the increase in APV and the short-lived decrease in pulse rate stability, so as to automatically trigger a CFR measurement without requiring any user interaction. For example, once injection is detected, the baseline APV value can be sampled a few seconds prior to injection, and the peak APV level can be found by application of a running maximum algorithm over the APV signal. CFR is then obtained by dividing the peak APV level by the baseline APV level and may be displayed fully automatically.

In the bottom graph of FIG. 6, the APV is calculated based on the IPV and instantaneous heart cycle period. At each time point, the APV is obtained by averaging the IPV a duration spanning 3 times the instantaneous heart cycle period (i.e. over the most recent X heart beats where X=3).

FIG. 7 shows a graph 350 with an IPV curve 352 and two differently obtained APV signals overlaid to an ultrasound (Doppler) spectrum 354. In FIG. 7, the APV waveform is overlaid on the Doppler spectrum 354 image along with the IPV 352. Shown are two APV waveforms that were obtained by different values for X (the number of heart cycles over which the IPV is averaged). FIG. 7 indicates the IPV curve 352 and APV signals overlaid over the Doppler spectrum for a limited time segment in FIG. 6. The APV is obtained in two methods, by averaging over the most recent one heart cycle (leading to a first APV curve 356) and the most recent heart cycles (leading to a second curve 358). A horizontal axis 360 indicates time and a left vertical axis 362 indicates velocity. A vertical index 364 on the right side indicates a grey value index.

From a portion 366 of the graph, a point in time of the adenosine injection can be retrieved.

The term "subject" may also be referred to as individual. The "subject" may further also be referred to as patient, although it is noted that this term does not indicate whether any illness or disease is actually present with the subject.

In another example, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

In an example, a computer program or program element for controlling an apparatus according to one of the examples above is provided, which program or program element, when being executed by a processing unit, is adapted to perform the method steps of one of the method examples above.

In another example, a computer readable medium having stored the program element is provided.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for flow measurement in a vessel, the device comprising:
  electronic storage configured to store a plurality of electrical ultrasound signals that relate to blood flow within the vessel;
  a data input;
  a processor; and
  an output device that outputs an output interface;
  wherein the data input is configured to provide the plurality of electrical ultrasound signals to the electronic storage and/or the processor, wherein the data input is configured to provide the plurality of electrical ultrasound signals obtained from an interventional device configured to be inserted into the vessel, wherein the processor is configured to:
    generate blood flow velocity data based on the plurality of electrical ultrasound signals;
    detect a measure for similarity or variation based on the plurality of electrical ultrasound signals;
    ascertain a pulse rate based on the detected measure for similarity or variation;
    compute, based on the pulse rate, an average parameter value for a blood flow parameter, which blood flow parameter is generated from the plurality of electrical ultrasound signals; and
    output, via the output interface, the average parameter value; and
  wherein the output interface is configured to present the average parameter value to a user.

2. The device according to claim 1, wherein the output device is a display.

3. The device according to claim 1, wherein the processor is configured to apply an autocorrelation scheme to the plurality of electrical ultrasound signals to determine a dependency of the signals and to generate time-related average values for the blood flow parameter.

4. The device according to claim 1, wherein, for the blood flow parameter, the processor is configured to estimate peak velocities in the vessel for a sequence of points in time based on the blood flow velocity data; and wherein, for computing the average parameter value, based on the estimated peak velocities and the derived pulse rate, the processor is configured to generate an average peak velocity.

5. The device according to claim 4, wherein the processor is configured to ascertain the pulse rate based on the estimated peak velocities.

6. The device according to claim 1, wherein the data input is configured to provide the plurality of electrical ultrasound signals as a plurality of ultrasound Doppler signals relating to blood flow in a sample volume.

7. The device according to claim 1, wherein the plurality of electrical ultrasound signals are obtained from an ultrasound transducer of the interventional device;

wherein the plurality of electrical ultrasound signals originates from a plurality of positions within the vessel; and wherein the processor is configured to ascertain flow velocity spectra over a range of locations comprising the plurality of depths within the vessel for the generation of the blood flow velocity data.

8. The device according to claim 1, wherein the plurality of electrical ultrasound signals is provided as a data stream and the processor is configured to generate the average parameter as real-time assessment.

9. The device according to claim 1, wherein the processor is configured to provide the average parameter value single-source based.

10. The device according to claim 1, wherein the processor is configured to determine a quality of flow data.

11. A system for flow measurement in a vessel, the system comprising:

a device for flow measurement according to claim 1; and an interventional device provided with an ultrasound transducer at a distal portion of the interventional device;

wherein the interventional device is configured for data transfer to and/or from the device for flow measurement; and wherein the ultrasound transducer is configured to generate the plurality of electrical ultrasound signals, which are provided to the data input.

12. The device according to claim 1, wherein the processor is configured to audibly output, via the output device, the average parameter value.

13. A method of flow measurement in a vessel, the method comprising:

providing, by a data input, a plurality of electrical ultrasound signals that relate to blood flow within the vessel to a processor, wherein the plurality of electrical ultrasound signals is obtained from an interventional device configured to be inserted into the vessel;

generating, by the processor, blood flow velocity data based on the plurality of electrical ultrasound signals;

detecting, by the processor, a measure for similarity or variation based on the plurality of electrical ultrasound signals;

ascertaining, by the processor, a pulse rate based on the detected measure for similarity or variation;

computing, by the processor, based on the pulse rate, an average parameter value for a blood flow parameter, which blood flow parameter is generated from the plurality of electrical ultrasound signals; and presenting, by an output interface, the average parameter value to a user.

14. A computer readable medium having stored computer-readable instructions executable by a processor to:

generate blood flow velocity data based on a plurality of electrical ultrasound signals obtained from an interventional device configured to be inserted into the vessel;

detect a measure for similarity or variation based on the plurality of electrical ultrasound signals;

ascertain a pulse rate based on the detected measure for similarity or variation; and compute, based on the pulse rate, an average parameter value for a blood flow parameter, which blood flow parameter is generated from the plurality of electrical ultrasound signals.

* * * * *